United States Patent
Nakanishi

(10) Patent No.: US 9,008,262 B2
(45) Date of Patent: Apr. 14, 2015

(54) X-RAY CT APPARATUS AND IMAGE PROCESSING APPARATUS

(71) Applicant: Satoru Nakanishi, Utsunomiya (JP)

(72) Inventor: Satoru Nakanishi, Utsunomiya (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 0 days.

(21) Appl. No.: 13/720,184

(22) Filed: Dec. 19, 2012

(65) Prior Publication Data
US 2013/0129037 A1 May 23, 2013

Related U.S. Application Data

(63) Continuation of application No. PCT/JP2012/075830, filed on Oct. 4, 2012.

(30) Foreign Application Priority Data

Oct. 12, 2011 (JP) ................................ 2011-225260

(51) Int. Cl.
| | |
|---|---|
| *G01N 23/083* | (2006.01) |
| *G06K 9/44* | (2006.01) |
| *G06K 9/60* | (2006.01) |
| *G06T 11/00* | (2006.01) |
| *G01N 23/04* | (2006.01) |
| *A61B 6/03* | (2006.01) |
| *A61B 6/00* | (2006.01) |

(52) U.S. Cl.
CPC ............ *G06T 11/003* (2013.01); *G01N 23/046* (2013.01); *A61B 6/032* (2013.01); *A61B 6/5205* (2013.01); *Y10S 378/901* (2013.01)

(58) Field of Classification Search
CPC .................. G06T 11/005; G06T 5/002; G06T 2207/20182; G06K 9/40; G06K 9/44; G01N 29/449
USPC .............. 378/4–20, 91, 98, 98.8, 98.12, 204, 378/210, 901; 382/128, 131, 254, 260, 264, 382/266, 269, 275
See application file for complete search history.

(56) References Cited

U.S. PATENT DOCUMENTS

| | | | |
|---|---|---|---|
| 6,608,942 B1 * | 8/2003 | Le | 382/279 |
| 6,819,734 B2 * | 11/2004 | Raupach | 378/4 |
| 2003/0103595 A1 | 6/2003 | Raupach | |
| 2011/0116594 A1 | 5/2011 | Yamakawa et al. | |

FOREIGN PATENT DOCUMENTS

| | | |
|---|---|---|
| JP | 64-64630 | 3/1989 |
| JP | 2004-230030 | 8/2004 |
| JP | 2005-6832 A | 1/2005 |
| JP | 2006-51202 | 2/2006 |
| WO | 2010/038536 A1 | 4/2010 |

OTHER PUBLICATIONS

International Search Report mailed on Nov. 6, 2012, issued for International Application No. PCT/JP2012/075830, filed on Oct. 4, 2012 (with English translation of the categories).
International Written Opinion mailed on Nov. 6, 2012, issued for International Application No. PCT/JP2012/075830, filed on Oct. 4, 2012.
English translation of the International Preliminary Report on Patentability and Written Opinion issued Apr. 24, 2014, in PCT/JP2012/075830, filed Oct. 4, 2012.
Office Action issued Oct. 17, 2014 in Chinese Patent Application No. 201280001604.7 (with English translation).

\* cited by examiner

*Primary Examiner* — Anastasia Midkiff
(74) *Attorney, Agent, or Firm* — Oblon, McClelland, Maier & Neustadt, L.L.P.

(57) ABSTRACT

According to one embodiment, an X-ray CT apparatus includes an generation unit, detection unit, processing unit, and reconstruction unit. The generation unit irradiates an object with X-rays. The detection unit includes detection elements corresponding to a plurality of channels, which output detection signals upon detecting X-rays. The processing unit smoothes projection data constituted by numerical values corresponding to signals output from the elements so as to more strongly smooth a portion exhibiting a larger amount of change in the numerical value. The reconstruction unit reconstructs an image by using a plurality of projection data smoothed by the image processing unit.

6 Claims, 3 Drawing Sheets

X-RAY CT APPARATUS AND IMAGE PROCESSING APPARATUS

CROSS-REFERENCE TO RELATED APPLICATIONS

This application is a Continuation Application of PCT Application No. PCT/JP2012/075830, filed Oct. 4, 2012 and based upon and claiming the benefit of priority from Japanese Patent Application No. 2011-225260, filed Oct. 12, 2011, the entire contents of all of which are incorporated herein by reference.

FIELD

Embodiments described herein relate generally to an X-ray CT (Computed Tomography) apparatus which captures a tomographic image by irradiating an object with X-rays and an image processing apparatus which processes the image captured by the X-ray CT apparatus.

BACKGROUND

An X-ray CT apparatus is designed to rotate an X-ray source and an X-ray detector around the body axis of an object, cause the X-ray source to irradiate the object with X-rays, and reconstruct a tomographic image based on the projection data obtained by detecting the X-rays transmitted through the object using the X-ray detector. This apparatus plays an important role in various medical practices such as disease diagnoses and medical and surgical planning.

The projection data obtained by an X-ray CT apparatus is discrete data, and hence aliasing artifacts occur more or less in reconstructed images. As methods of preventing the occurrence of such artifacts, there have been proposed a method (flying focal spot technique) of apparently reducing a channel pitch to ½ by executing data acquisition concerning the same slice plane for each focus by using an X-ray source having two focuses, an offset method (QQ offset technique) of offsetting the center position of the X-ray detector relative to the imaging center line connecting the focus and the rotation axis by a distance corresponding to a fraction of a channel pitch, and a method of applying an LPF (Low Pass Filter) to projection data.

The above flying focal spot technique requires a dedicated X-ray tube, and hence it is not easy to introduce this technique. In addition, according to the QQ offset technique, when using an apparatus having a cone angle such as an AD (Area Detecting) CT, since real data and counter data do not exist on the same plane around this cone angle, it is not possible to obtain ideal counter data. Under the circumstances, a method using a low pass filter is often used as a main approach to reduce aliasing artifacts.

Although artifacts are reduced by uniformly applying a low pass filter to the entire region of projection data, the resolution of a reconstructed image decreases to impair granularity.

It is an object to provide an X-ray CT apparatus and image processing apparatus which can reduce artifacts in a reconstructed image while maintaining the resolution of the reconstructed image by using a simple method.

DETAILED DESCRIPTION

Figure 1:
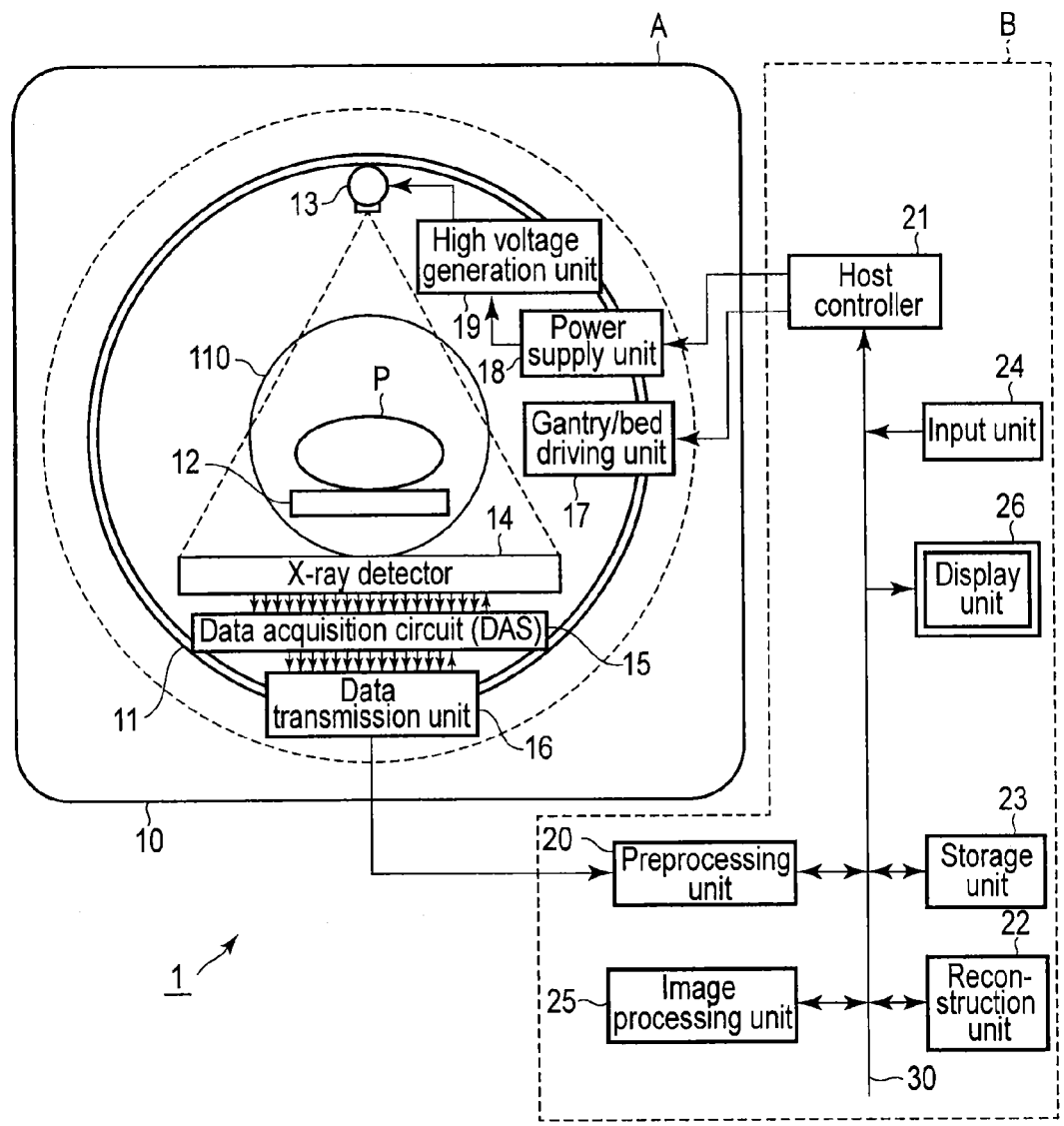
FIG. 1 is a block diagram showing the overall arrangement of an X-ray CT apparatus according to an embodiment.

In general, according to one embodiment, an X-ray CT apparatus includes an X-ray generation unit, X-ray detection unit, image processing unit, and reconstruction unit.

The X-ray generation unit irradiates an object with X-rays. The X-ray detection unit includes X-ray detection elements corresponding to a plurality of channels, which are arrayed in a predetermined direction to output detection signals upon detecting X-rays transmitted through the object. The image processing unit smoothes projection data constituted by numerical values corresponding to detection signals output from the X-ray detection elements corresponding to the plurality of channels so as to more strongly smooth a portion exhibiting a larger amount of change in the numerical value. The reconstruction unit reconstructs an image by using a plurality of projection data smoothed by the image processing unit.

Several embodiments will be described below with reference to the accompanying drawing. Note that the same reference numerals in the following description denote constituent elements having almost the same functions and arrangements, and a repetitive description will be made only when required.

First Embodiment

The first embodiment will be described first.
[Overall Arrangement of X-Ray CT Apparatus]

FIG. 1 is a block diagram showing the overall arrangement of an X-ray CT apparatus 1 according to this embodiment. As shown in FIG. 1, the X-ray CT apparatus 1 includes a gantry device A and a console device B.

The gantry device A irradiates an object with X-rays and acquires projection data (or raw data) by detecting the X-rays transmitted through the object. Note that X-ray CT systems include various types, e.g., a rotate/rotate type in which an X-ray tube and an X-ray detector system rotate together around an object, and a stationary/rotate type in which many detection elements are arrayed in the form of a ring, and only an X-ray tube rotates around an object. The embodiments can be applied to either type. In this case, a rotate/rotate type X-ray CT apparatus, which is currently the mainstream, will be exemplified.

As shown in FIG. 1, the gantry device A includes a fixed unit 10, a rotating unit 11, a bed 12, an X-ray tube 13, an X-ray detector 14, a data acquisition circuit (DAS) 15, a data transmission unit 16, a gantry/bed driving unit 17, a power supply unit 18, and a high voltage generation unit 19.

The X-ray tube 13 is a vacuum tube which generates X-rays and is provided on the rotating unit 11.

The X-ray detector 14 is an X-ray detection unit which detects the X-rays transmitted through an object P and is mounted on the rotating unit 11 in a direction to face the X-ray tube 13.

Figure 2:
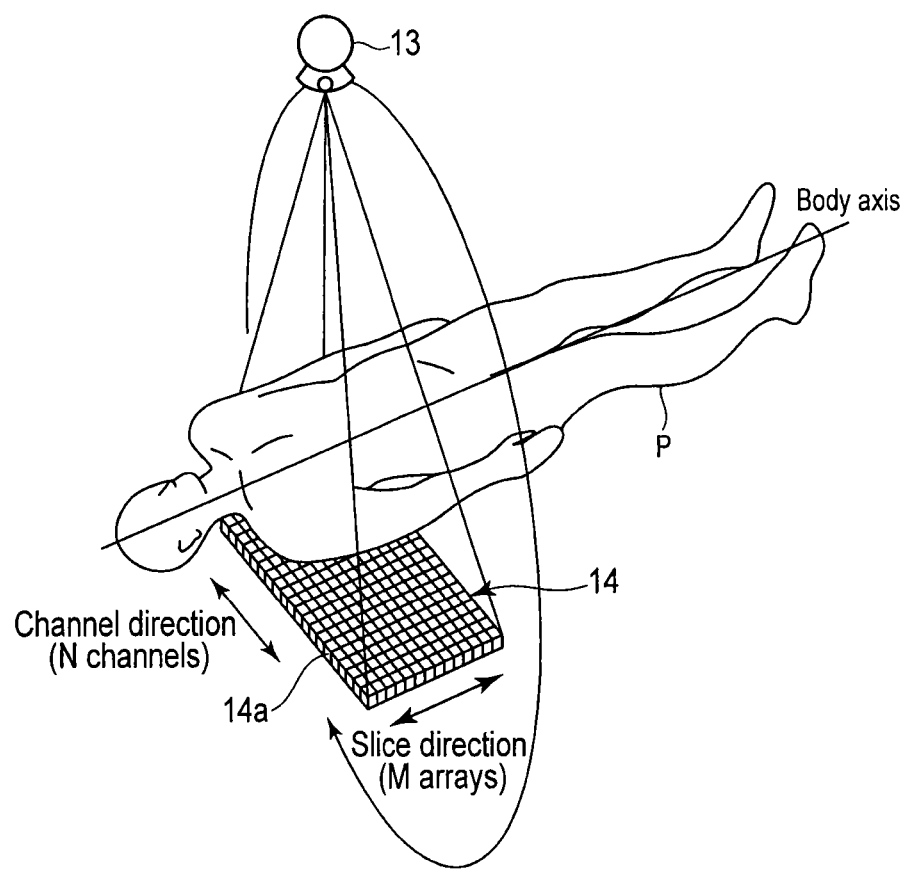
FIG. 2 is a view showing X-ray detection elements of an X-ray detector according to an embodiment.

As shown in FIG. 2, the X-ray detector 14 is formed by providing, in the slice direction along the body axis of the object P, M arrays of X-ray detection elements corresponding to N channels which are arrayed in the channel direction almost perpendicular to the body axis of the object P. Each X-ray detection element 14a includes a phosphor such as a scintillator which converts, for example, X-rays into light, and a photoelectric conversion element such as a photodiode which converts the light into charge (electrical signal).

The rotating unit 11 is provided with an opening portion 110, in which the bed 12 is disposed. The object P is placed on the slide top of the bed 12. The gantry/bed driving unit 17 moves the bed 12 in the body axis direction described above while rotating the rotating unit 11 at high speed around a central axis parallel to the body axis direction of the object P inserted into the opening portion 110. In this manner, the object P is scanned over a wide range.

The data acquisition circuit 15 includes a plurality of data acquisition elements on which DAS chips are arranged, receives large amounts of data concerning all the N (channels)×M (arrays) X-ray detection elements which are detected by the X-ray detector 14 (N (channels)×M (arrays) data per view will be referred to as "projection data" hereinafter), and collectively transmits the data having undergone amplification processing, A/D conversion processing, and the like in block to the fixed unit 10 side via the data transmission unit 16 using optical communication.

The fixed unit 10 receives operating power from an external power source such as a commercial AC power source. The operating power supplied to the fixed unit 10 is transferred to the respective units of the rotating unit 11 via the power supply unit 18 which is, for example, a slip ring.

The high voltage generation unit 19 includes a high voltage transformer, a filament heating converter, a rectifier, and a high voltage switch. The high voltage generation unit 19 transforms the operating power supplied from the power supply unit 18 into a high voltage and applies it to the X-ray tube 13.

The console device B will be described next. The console device B includes a preprocessing unit 20, a host controller 21, a reconstruction unit 22, a storage unit 23, an input unit 24, an image processing unit 25, a display unit 26, and a data/control bus 30.

The preprocessing unit 20 receives projection data from the data acquisition circuit 15 via the data transmission unit 16 and performs sensitivity correction and X-ray intensity correction for the data.

The host controller 21 performs comprehensive control concerning imaging processing, data processing, and image processing.

The reconstruction unit 22 generates reconstructed image data corresponding to a predetermined slice by performing reconstruction processing for projection data based on predetermined reconstruction parameters (a reconstruction region size, reconstruction matrix size, threshold for extraction of a region of interest, and the like).

The storage unit 23 stores various data such as projection data before and after the application of various types of correction by the preprocessing unit 20 and reconstructed image data.

The input unit 24 includes a keyboard, various types of switches, and mouse and is used to input various kinds of scan conditions such as a slice thickness and the number of slices.

The image processing unit 25 performs the processing of removing high-frequency noise from the projection data output from the preprocessing unit 20 (see FIG. 3), window conversion for the reconstructed image data generated by the reconstruction unit 22, and image processing such as RGB processing. The image processing unit 25 generates a tomographic image of an arbitrary slice, a projection image from an arbitrary direction, and a pseudo three-dimensional image such as a three-dimensional surface image, and outputs them to a display unit 26. The display unit 26 displays the output image data as X-ray CT images.

The data/control bus 30 is a signal line which connects the respective units to transmit/receive various kinds of data, control signals, address information, and the like.

Note that constituent elements of the X-ray CT apparatus 1 which are associated with image processing, such as the image processing unit 25 and the reconstruction unit 22, constitute an image processing apparatus according to this embodiment.

The operation of the X-ray CT apparatus 1 (or image processing apparatus) having the above arrangement will be described next.

Aliasing artifacts due to mainly undersampling in the channel direction occur in the image reconstructed based on the projection data captured by the X-ray detector 14 as shown in FIG. 2.

In order to remove such artifacts, the X-ray CT apparatus 1 according to this embodiment smoothes projection data constituted by numerical values corresponding to the detection signals output from the X-ray detection elements 14a corresponding to the N channels so as to more strongly smooth data portions exhibiting larger amounts of change in the numerical values, and reconstructs an image by using a plurality of projection data after smoothing. This operation will be described in detail below with reference to the flowchart of FIG. 3.

Figure 3:
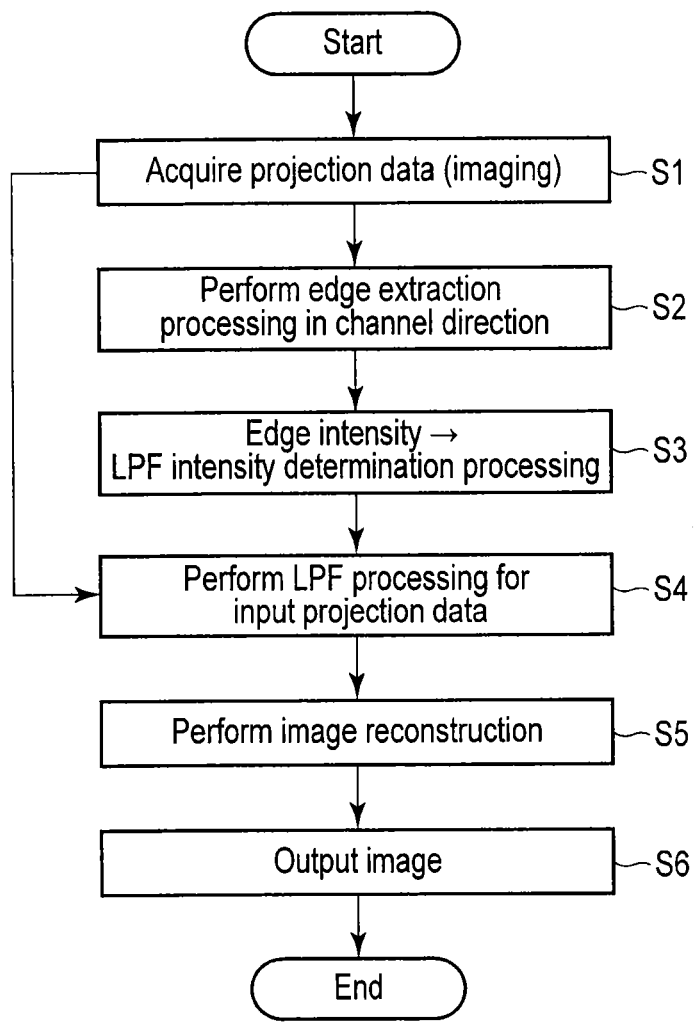
FIG. 3 is a flowchart for explaining the operation of an X-ray CT apparatus according to an embodiment.

The processing shown in the flowchart shown in FIG. 3 starts when, for example, a doctor or a technician issues an instruction to execute X-ray imaging by operating the input unit 24.

At the beginning of this processing, first of all, the host controller 21 controls the gantry/bed driving unit 17 to rotate the rotating unit 11, and applies a voltage to the X-ray tube 13 via the power supply unit 18 and the high voltage generation unit 19 to generate X-rays, thereby scanning the object P (step S1). At this time, N (channels)×M (arrays) projection data in a plurality of views (imaging angles) are sent to the preprocessing unit 20 via the data acquisition circuit 15, the data transmission unit 16, and the like and stored in the storage unit 23 through various types of correction.

In order to remove the above artifacts appearing in the reconstructed image, the processing in steps S2 to S4 is executed for numerical values of the respective projection data strings (1 to M) in each view stored in the storage unit 23 in step S1.

That is, first of all, the image processing unit 25 extracts the intensities of edges of a string as a processing target (amounts of change in numerical values constituting the string) in the channel direction (step S2). In this case, if input data In[ch] (ch=1 to N) represents each numerical value of a string as a processing target, edge intensity Edge[ch] of each portion of input data In[ch] is represented by equation (1) given below:

$$Edge[ch] = ABS(In[ch-1] - In[ch+1]) \qquad (1)$$

The method to be used is not limited to this, and it is possible to use any method as long as it can extract the amount of change of input data In[ch] in the channel direction in step S2. In addition, the processing of extracting edge intensities can be interpreted as HPF (High Pass Filter) processing, which is susceptible to noise. In consideration of this, LPF (Low Pass Filter) processing may be performed for each projection data in the channel direction as preprocessing for edge intensity processing.

Upon obtaining edge intensity Edge[ch], the image processing unit 25 determines the intensity of LPF processing to be performed for input data In[ch] (step S3). In this case, the image processing unit 25 obtains LPF intensity S[ch] that smoothes input data In[ch] so as to more strongly smooth data portions exhibiting larger values of edge intensity Edge[ch] obtained in step S2. More specifically, the image processing unit 25 defines in advance a conversion function for converting edge intensity Edge[ch] into LPF intensity S[ch] and obtains LPF intensity S[ch] in accordance with the function. As the above conversion function, it is possible to use any type of function which monotonically increases LPF intensity S[ch] in accordance with edge intensity Edge[ch]. This embodiment uses a sigmoid function represented by equation (2) given below:

$$S[ch]=1/(1+\exp(-a*(Edge[ch]-b))) \quad (2)$$

where "a" and "b" are parameters which are determined experimentally, empirically, or logically to maximize the artifact reduction effect in the reconstructed image and minimize adverse effects such as a deterioration in granularity.

Upon obtaining LPF intensity S[ch], the image processing unit 25 performs LPF processing for input data In[ch] by using LPF intensity S[ch] (step S4).

In LPF processing in this embodiment, convolution between input data In[ch] and a Gaussian filter implements the LPF processing in step S4.

When using a Gaussian filter, the variance of a Gaussian distribution is made to be proportional to LPF intensity S[ch]. That is, if a variance corresponding to each channel ch (=1 to N) is represented by V[ch], a Gaussian shape is determined by equation (3) given below:

$$V[ch]=C*S[ch] \quad (3)$$

where "C" is a parameter which is determined experimentally, empirically, or logically to maximize the artifact reduction effect in the reconstructed image and minimize adverse effects such as a deterioration in granularity. According to equations (2) and (3), a large value of variance V[ch] is obtained for a portion having a large value of edge intensity Edge[ch].

If the result obtained by performing LPF processing for input data In[ch] is represented by output data Out[ch] and Gaussian (Gaussian function) average μ=0.0, output data Out[ch] is represented by a convolution between In[ch] and the Gaussian as given by equation (4).

$$Out[ch]=In[ch] \otimes Gaussian(\sigma^2=V[ch], \mu=0.0) \quad (4)$$

If LPF intensity S[ch]=0, since no Gaussian can be defined, the LPF processing based on equation (4) is not performed.

In step S4, the image processing unit 25 obtains output data Out[ch] by performing the computation based on equations (3) and (4), and stores obtained output data Out[ch] in the storage unit 23. Note that since a concrete method of computing a convolution between input data to be processed (In[ch] in this embodiment) and a Gaussian is known in the field of image engineering, a description of the computation process based on equation (4) will be omitted.

After the image processing unit 25 executes the processing in steps S2 to S4 for the respective components of the respective strings (1 to M) of projection data in each view stored in the storage unit 23 in step S1, the reconstruction unit 22 generates reconstructed image data by performing a predetermined reconstruction method using projection data (projection data formed from Out[ch] described above) in each view after the application of LPF processing which are stored in the storage unit 23, and stores the generated data in the storage unit 23 (step S5).

Subsequently, the image processing unit 25 generates a tomographic image of an arbitrary slice, a projection image from an arbitrary direction, a pseudo three-dimensional image, or the like based on the reconstructed image data stored in the storage unit 23, and outputs the generated data to the display unit 26 (step S6). The display unit 26 displays the output image data as an X-ray CT image. With the above operation, the apparatus completes a series of processing shown in the flowchart.

As described above, this embodiment extracts edge intensity Edge[ch] in the channel direction from each string (1 to M) of the projection data acquired by the data acquisition circuit 15, and obtains LPF intensity S[ch] corresponding to each extracted edge intensity. The embodiment then obtains output data Out[ch] by performing a convolution between a Gaussian filter using a value proportional to obtained LPF intensity S[ch] as variance V[ch] and input data In[ch].

Applying LPF processing to projection data will smooth the projection data so as to more strongly smooth portions exhibiting larger changes in the channel direction. That is, this processing strongly smoothes portions which become causes of aliasing artifacts and maintain the values of the original data of the remaining portions as much as possible. Aliasing artifacts are reduced or eliminated in an image reconstructed based on projection data after such LPF processing. In addition, the intensity of LPF processing is low at portions irrelevant to aliasing artifacts, and hence the granularity of the image is maintained. Therefore, the resolution does not unnecessarily degrade.

Second Embodiment

The second embodiment will be described next.

This embodiment differs from the first embodiment in that it obtains output data Out[ch] by performing weighted addition of input data In[ch] and the data obtained by applying LPF processing to input data In[ch] instead of using convolution with a Gaussian filter.

The arrangement shown in FIGS. 1 and 2 and the processing procedure shown in FIG. 3 are the same as those in the first embodiment. In step S4, an image processing unit 25 obtains output data Out[ch] by the following procedure.

That is, the image processing unit 25 uniformly applies LPF processing to input data In[ch]. The result obtained by applying this LPF processing to the data is represented by LPF data LPF_In[ch]. This processing uses a convolution of a three-point filter such that the data obtained by performing weighted addition of input data In[ch−1], In[ch], and In[ch+1] with ratios of 0.3, 0.4, and 0.3 is used as LPF data LPF_In[ch]. Note that LPF processing to be used in this case may be any type of method as long as it is of a shift-invariant type in the channel direction.

The image processing unit 25 then obtains output data Out[ch] by adding input data In[ch] and LPF data LPF_In[ch] with weights based on LPF intensity S[ch] in step S3 according to equation (5) given below:

$$Out[ch]=(1.0-S[ch])*In[ch]+S[ch]*LPF\_In[ch] \quad (5)$$

Even if output data Out[ch] is obtained in this manner, since projection data is smoothed while portions exhibiting larger changes in numerical value in the channel direction are smoothed more strongly, the same effects as those in the first embodiment can be obtained.

Modification

A method of extracting edge intensity Edge[ch] in step S2, a method of deriving LPF intensity S[ch] from edge intensity Edge[ch] in step S3, and a method of applying LPF processing to projection data (In[ch]) with an intensity corresponding to LPF intensity S[ch] in step S4 are not limited to those disclosed in each embodiment described above. These methods can be replaced by various types of methods which can be conceived by those skilled in the art.

Each embodiment described above has exemplified the X-ray CT apparatus 1 including the X-ray detector 14 having the N (channels)×M (arrays) X-ray detection elements. However, the method indicated by the flowchart of FIG. 3 can be applied to even a so-called single CT including an X-ray detector having only one array (M=1) of X-ray detection elements.

In each embodiment described above, the image processing unit 25 and the reconstruction unit 22 in the X-ray CT apparatus 1 execute the processes in steps S2 to S6 shown in the flowchart of FIG. 3 and the like. However, an image processing apparatus separate from the X-ray CT apparatus 1 may execute part or all of these processes. In this case, as the above image processing apparatus, it is possible to use a personal computer or a server connected to a network in a hospital or various types of apparatuses such as a dedicated computer system configured to execute part or all of the processes in steps S2 to S6. In addition, projection data to be processed by this image processing apparatus may be read out from the storage unit 23 in the X-ray CT apparatus 1, or stored in the storage unit provided in the image processing apparatus, or read out from a storage medium such as a CD-ROM or a USB memory.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus comprising:
an X-ray generation unit configured to irradiate an object with X-rays;
an X-ray detection unit including X-ray detection elements corresponding to a plurality of channels, which are arrayed in a predetermined direction to output detection signals upon detecting X-rays transmitted through the object;
an image processing unit configured to smooth projection data constituted by numerical values corresponding to detection signals output from the X-ray detection elements corresponding to the plurality of channels so that for all values of a change in the numerical value in a channel direction, the greater the change in the numerical values in the channel direction, the greater a smoothing strength to the projection data; and
a reconstruction unit configured to reconstruct an image by using a plurality of projection data smoothed by the image processing unit.

2. The X-ray CT apparatus of claim 1, wherein the image processing unit smoothes the projection data by applying a Gaussian filter to the projection data so that the greater the change in the numerical values in the channel direction, the greater a variance value.

3. The X-ray CT apparatus of claim 1, wherein the image processing unit smoothes the projection data by uniformly smoothing the projection data and adding the each of the numerical values included in the uniformly smoothed projection data and corresponding numerical values included in the projection data so that the greater the change in the numerical values, the smaller a weight to the projection data.

4. An image processing apparatus comprising:
an image processing unit configured to smooth projection data constituted by numerical values corresponding to detection signals output when X-ray detection elements corresponding to a plurality of channels, which are arrayed in a predetermined direction, detect X-rays transmitted through an object, so that for all values of a change in the numerical value in a channel direction, the greater the change in the numerical values in the channel direction, the greater a smoothing strength to the projection data; and
a reconstruction unit configured to reconstruct an image by using a plurality of projection data smoothed by the image processing unit.

5. The image processing apparatus of claim 4, wherein the image processing unit smoothes the projection data by applying a Gaussian filter to the projection data so that the greater the change in the numerical values in the channel direction, the greater a variance value.

6. The image processing apparatus of claim 4, wherein the image processing unit smoothes the projection data by uniformly smoothing the projection data and adding the each of the numerical values included in the uniformly smoothed projection data and corresponding numerical values included in the projection data so that the greater the change in the numerical values, the smaller a weight to the projection data.

* * * * *